US00PP24405P2

(12) United States Plant Patent
Hooijman

(10) Patent No.: US PP24,405 P2
(45) Date of Patent: Apr. 29, 2014

(54) ROSE PLANT NAMED 'ESM R068'

(50) Latin Name: *Rosa hybrida*
Varietal Denomination: Esm R068

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 141 days.

(21) Appl. No.: 13/506,270

(22) Filed: Apr. 7, 2012

(51) Int. Cl.
*A01H 5/00* (2006.01)

(52) U.S. Cl.
USPC ..... Plt./140

(58) Field of Classification Search
USPC ..... Plt./140, 139, 108, 151, 150
See application file for complete search history.

*Primary Examiner* — Howard Locker
(74) *Attorney, Agent, or Firm* — C. A. Whealy

(57) ABSTRACT

A new and distinct cultivar of Rose plant named 'Esm R068', characterized by its upright, long and strong flowering stems; vigorous growth habit and high productivity; red-colored flowers that are typically grown as single stems; and excellent postproduction longevity.

1 Drawing Sheet

Botanical designation: *Rosa hybrida.*
Cultivar denomination: 'ESM R068'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'Esm R068'.

The new Rose plant is a product of a planned breeding program conducted by the Inventor in El Quinche, Pichincha, Ecuador. The objective of the breeding program was to develop new cut flower Rose varieties with red-colored flowers and excellent postproduction longevity.

The new Rose plant originated from a cross-pollination made by the Inventor in May, 2007 of a proprietary Rose selection identified as Line 17, not patented, as the female, or seed, parent with a proprietary Rose selection identified as Line 299, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in April, 2008.

Asexual reproduction of the new Rose plant by bud grafting in El Quinche, Pichincha, Ecuador since July, 2008 has shown that the unique features of this new Rose plant are stable and reproduced true to type in successive generations of asexual reproduction.

SUMMARY OF THE INVENTION

Plants of the new Rose have not been observed under all possible environmental conditions and cultural practices. The phenotype may vary somewhat with variations in environmental conditions such as temperature and light intensity, without however, any variance in genotype.

The following traits have been repeatedly observed and are determined to be the unique characteristics of 'Esm R068'. These characteristics in combination distinguish 'Esm R068' as a new and distinct Rose plant:

1. Upright, long and strong flowering stems.
2. Vigorous growth habit and high productivity.
3. Red-colored flowers that are typically grown as single stems.
4. Excellent postproduction longevity.

Plants of the new Rose differ from plants of the female parent selection in the following characteristics:

1. Plants of the new Rose are taller than plants of female parent selection.
2. Plants of the new Rose are more productive than plants of female parent selection.
3. Flowering stems of plants of the new Rose have fewer thorns than flowering stems of plants of the female parent selection.
4. Plants of the new Rose have larger flowers than plants of the female parent selection.
5. Plants of the new Rose and the female parent selection differ in flower color as plants of the female parent selection have orange and pink bi-colored flowers.

Plants of the new Rose differ from plants of the male parent selection in the following characteristics:

1. Plants of the new Rose are more productive than plants of the male parent selection.
2. Plants of the new Rose and the male parent selection differ in flower color as plants of the male parent selection have red and lighter red bi-colored flowers.

Plants of the new Rose can be compared to plants of Rose 'Freedom', not patented. In side-by-side comparisons conducted in El Quinche, Pichincha, Ecuador, plants of the new Rose differed from plants of 'Freedom' in the following characteristics:

1. Plants of the new Rose were more vigorous than plants of 'Freedom'.
2. Plants of the new Rose were broader than plants of 'Freedom'.
3. Plants of the new Rose had shorter internodes than plants of 'Freedom'.
4. Plants of the new Rose had stronger flowering stems than plants of 'Freedom'.

5. Plants of the new Rose and 'Freedom' differed in stem color as plants of 'Freedom' had green-colored stems.
6. Plants of the new Rose flowered earlier than plants of 'Freedom'.
7. Flowers of plants of the new Rose were larger with fewer petals than flowers of plants of 'Freedom'.
8. Flowers of plants of the new Rose were longer lasting than flowers of plants of 'Freedom'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the left of the sheet comprises a side perspective view of typical flowering stem of 'Esm R068'.

The photograph at the upper right of the sheet is a close-up view of a typical flower of 'Esm R068'.

The photographs at the bottom right of the sheet are close-up views of the upper and lower surfaces of typical leaves of 'Esm R068'.

DETAILED BOTANICAL DESCRIPTION

Plants of the new Rose have not been observed under all possible environmental conditions and cultural practices. The phenotype may vary somewhat with variations in environmental conditions such as temperature and light intensity, without, however, any variance in genotype. The aforementioned photographs, following observations and measurements describe plants grown in 10-liter containers in a polyethylene-covered greenhouse in El Quinche, Pichincha, Ecuador and under typical hydroponic Rose production practices. Plants were pinched about 13 to 14 weeks after planting. Plants were 61 weeks old when the photographs and detailed description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm R068'.

Parentage:

*Female, or seed, parent*.—Proprietary seedling selection of *Rosa hybrida* identified Line 17, not patented.

*Male, or pollen, parent*.—Proprietary seedling selection of *Rosa hybrida* identified Line 299, not patented.

Propagation:

*Type*.—By bud grafting.

*Time to initiate roots*.—About seven to ten days at 26° C. to 30° C.

*Time to produce a rooted young plant*.—About four to five weeks at 22° C. to 26° C.

*Root description*.—Fibrous, medium in thickness; close to 200B in color.

*Rooting habit*.—Freely branching; dense.

Plant description:

*Plant and growth habit*.—Perennial shrub; upright, long and strong flowering stems; typically grown as a single-stem cut flower; vigorous growth habit.

*Branching habit*.—Freely basal branching habit; highly productive with about 10.8 to 12 flowering stems developing per plant per year.

*Plant height*.—About 137 cm.

*Plant width* (*spread*).—About 56 cm.

*Lateral branches* (*peduncles*).—Length: About 98 cm. Diameter: About 8 mm. Internode length: About 5.6 cm. Texture: Smooth, glabrous; older stems, woody. Color: Close to N199A to N199B. Thorns: Density: Medium density. Shape: Triangular with sharp acuminate apices; slightly incurved. Height: About 7 mm. Length, at base: About 1.2 cm. Color, immature: Close to 176A and 199C. Color, mature: Close to 177A and 164A.

Foliage description:

*Arrangement*.—Alternate; compound with typically seven leaflets per leaf.

*Leaf length*.—About 18.9 cm.

*Leaf width*.—About 13.1 cm.

*Terminal leaflet length*.—About 7.6 cm.

*Terminal leaflet width*.—About 5.2 cm.

*Lateral leaflet length*.—About 6.3 cm.

*Lateral leaflet width*.—About 4.5 cm.

*Leaflet shape*.—Ovate.

*Leaflet apex*.—Acuminate.

*Leaflet base*.—Attenuate.

*Leaflet margin*.—Serrate.

*Leaflet texture, upper and lower surfaces*.—Smooth, glabrous; coriaceous.

*Leaflet venation pattern*.—Pinnate.

*Leaflet color*.—Developing leaflets, upper surface: Close to 139A and 187A. Developing leaflets, lower surface: Close to 147A, 146B and 187A. Fully expanded leaflets, upper surface: Between 139A and 147A; venation, close to 152B. Fully expanded leaflets, lower surface: Close to 147B; venation, close to 148B.

*Petioles, leaves*.—Length: About 1.4 cm. Diameter: About 3 mm. Texture, upper surface: Prickly. Texture, lower surface: Smooth, glabrous. Color, upper surface: Close to 161B, 143C and 187A. Color, lower surface: Close to 144A and N199B.

*Petioles, leaflets*.—Length: About 2.2 cm. Diameter: About 2 mm. Texture, upper surface: Prickly. Texture, lower surface: Smooth, glabrous. Color, upper surface: Close to 146C and 187A. Color, lower surface: Close to 146C and N199B.

*Stipules*.—Arrangement and appearance: Two, adnate to the petiole, leafy in appearance. Length: About 3 cm. Width: About 3 mm. Shape: Roughly deltoid. Apex: Acuminate. Base: Truncate. Margin: Serrate. Texture, upper and lower surfaces: Smooth, glabrous; membranous; pubescence along the margins. Venation pattern: Pinnate. Color, upper surface: Close to 137A. Color, lower surface: Close to 144A.

Flower description:

*Flower type and flowering habit*.—Symmetrical rosette flowers; flowers typically grown as single stems; flowers face upright.

*Flowering season*.—Plants of the new Rose flower year-round under greenhouse conditions; early flowering habit, plants begin flowering about 67 to 70 days after pinching; in the garden, optimal flowering from spring through autumn; flowering intermittent.

*Flower diameter*.—About 13.3 cm.

*Flower depth* (*height*).—About 6.8 cm.

*Flower longevity on plant*.—About 34 days; flowers persistent.

*Flower longevity as a cut flower*.—Excellent postproduction longevity, flowers last about ten to twelve days.

*Fragrance*.—Very faintly fragrant, pleasant.

*Flower buds*.—Shape: Ovoid. Length: About 6.3 cm. Diameter: About 4.6 cm. Color: Close to 146B.

*Petals*.—Quantity: About 42 to 45 per flower; petals imbricate. Length: About 7.1 cm. Width: About 7.9 cm. Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Between 53A and 46A; towards the base, close to 162D. When opening, lower surface: Close to 46A. Fully opened, upper surface: Close to 53A to 53B; towards the base, close to 162C. Fully opened, lower surface: Close to 53A to 53C.

*Petaloids*.—Quantity: About nine; petaloids whorled. Length: Variable. Width: Variable. Shape: Irregularly shaped. Apex: Blunt to shortly acute. Base: Obtuse. Margin: Entire or uneven. Texture, upper and lower surfaces: Smooth, glabrous; papery to coriaceous. Color: When opening and fully opened, upper surface: Close to 45D; towards the base, close to 155C. When opening and fully opened, lower surface: Close to 46A; towards the base, close to 155C.

*Sepals*.—Quantity per flower: Typically five in a single whorl. Length: About 4.9 cm. Width: About 1.7 cm. Shape: Roughly deltoid. Apex: Tapered. Base: Truncate. Margin: Entire; ciliate and/or glandular. Texture, upper and lower surfaces: Coriaceous; pubescence along the margins. Color: When opening, upper surface: Close to 148D. When opening, lower surface: Between 144A and 146B. Fully opened, upper surface: Between 145B and 146C. Fully opened, lower surface: Close to 144A to 144B and 177A.

*Reproductive organs*.—Stamens: Quantity: About 260 per flower. Anther length: About 3 mm. Anther shape: Reniform. Anther color: Close to 24C. Filament color: Close to 53C. Pollen amount: Scarce. Pollen color: Close to 163A. Pistils: Quantity: About 229 per flower. Pistil length: About 1.6 cm. Stigma shape: Broadly reniform. Stigma color: Close to 162C. Style length: About 1.2 cm. Style color: Close to 150D tinted with close to 46B. Receptacle height: About 1.5 cm. Receptacle diameter: About 1.7 cm. Receptacle shape: Cup-shaped. Receptacle texture: Smooth, glabrous. Receptacle color: Close to 144A. Seeds and fruits: Seed and fruit development have not been observed on plants of the new Rose.

Pathogen & pest resistance: Plants of the new Rose have been observed to somewhat tolerant to Powdery Mildew and *Botrytis*. Plants of the new Rose have not been observed to be resistant to pests and other pathogens common to Rose plants.

Temperature tolerance: Plants of the new Rose have been observed to tolerate temperatures ranging from 0° C. to 35° C.

It is claimed:

1. A new and distinct Rose plant named 'Esm R068' as illustrated and described.

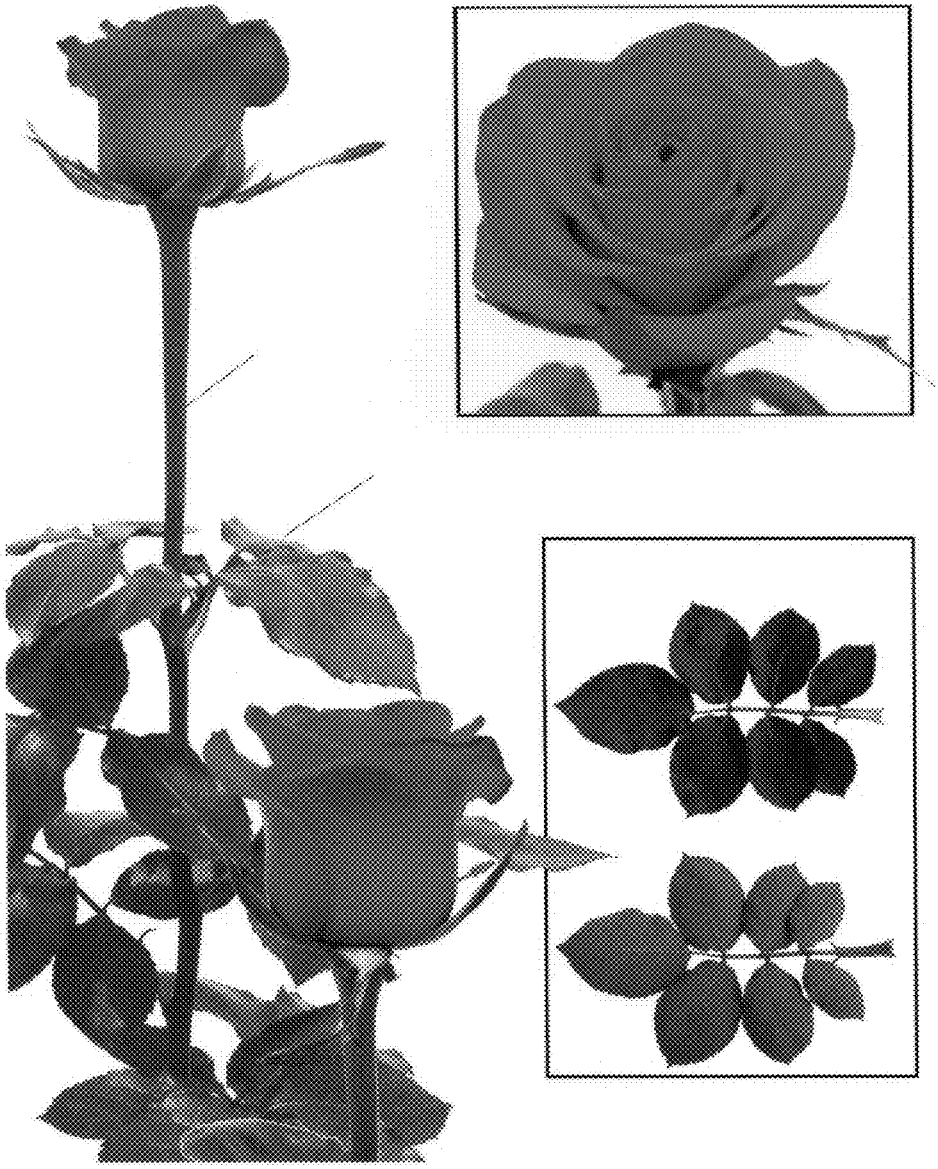

* * * * *